United States Patent [19]

Anis

[11] Patent Number: 4,479,802
[45] Date of Patent: Oct. 30, 1984

[54] IRRIGATING VECTIS

[76] Inventor: Aziz Y. Anis, 7531 N. Hampton, Lincoln, Nebr. 68506

[21] Appl. No.: 467,033

[22] Filed: Feb. 16, 1983

[51] Int. Cl.³ ............................................. A61M 5/00
[52] U.S. Cl. ................................................. 604/275
[58] Field of Search ............... 604/275, 276, 280, 281, 604/282

[56] References Cited

U.S. PATENT DOCUMENTS

| 2,483,851 | 10/1949 | Smith | 604/275 |
|---|---|---|---|
| 4,014,049 | 3/1977 | Richards | 3/13 |
| 4,159,546 | 7/1979 | Shearing | 3/13 |
| 4,174,543 | 11/1979 | Kelman | 3/13 |
| 4,244,060 | 1/1981 | Hoffer | 3/13 |
| 4,304,012 | 12/1981 | Richard | 3/13 |

FOREIGN PATENT DOCUMENTS

| 729861 | 1/1943 | Fed. Rep. of Germany | 604/275 |
| 25306 | of 1905 | United Kingdom | 604/275 |

OTHER PUBLICATIONS

Knolle-Pearce Irrigating Vectis, OP2079, OP2178, 1982.

Primary Examiner—John D. Yasko
Attorney, Agent, or Firm—Zarley, McKee, Thomte, Voorhees & Sease

[57] ABSTRACT

An irrigating vectis is described for use in the extraction of cataracts. The vectis comprises an elongated shank portion having one end thereof adapted to be connected to an irrigating syringe. An irrigating loop portion is provided at the other end of the shank portion. The loop portion comprises first and second loop members which extend from the shank portion in a diverging relationship, and an end portion extending between the first and second loop portions with the end portion having bulged portions at its end and an indented portion positioned therebetween.

1 Claim, 8 Drawing Figures

IRRIGATING VECTIS

BACKGROUND OF THE INVENTION

This invention relates to a vectis and more particularly to an irrigating vectis which is used during the extraction of cataracts. Typical of the type of irrigating vectis presently available is the vectis known as the Knolle-Pearce irrigating vectis which is distributed by American V. Mueller, a division of American Hospital Supply Corporation. The conventional irrigating vectis comprises an elongated shank having one end thereof adapted to be connected to an irrigating shank. The Knolle-Pearce irrigating vectis is provided with a generally oval-shaped closed loop portion at the other end of the shank portion. The closed loop portion is provided with three irrigating holes so that the irrigating solution can be ejected or discharged therefrom as the vectis is moved downwardly behind the nucleus of the lens of the eye. A difficulty encountered with the Knolle-Pearce irrigating vectis is the initial positioning of the vectis behind the upper portion of the nucleus of the lens. The positioning of the vectis behind the upper portion of the lens normally requires the use of two hands.

Therefore, it is a principal object of the invention to provide an improved irrigating vectis.

A further object of the invention is to provide an irrigating vectis which may be positioned behind the upper portion of the nucleus of the lens without the use of two hands.

Still another object of the invention is to provide an irrigating vectis having a closed loop portion with an indented portion positioned between a pair of spaced-apart bulged portions.

Still another object of the invention is to provide an irrigating vectis having a configuration such that as the vectis is moved upwardly over the upper portion of the lens, the lens tends to bulge outwardly or forwardly through an indented portion of the vectis, as the iris is retracted, which facilitates the positioning of the vectis behind the upper portion of the lens.

Still another object of the invention is to provide an irrigating vectis which is convenient to use.

These and other objects will be apparent to those skilled in the art.

SUMMARY OF THE INVENTION

Figure 1:
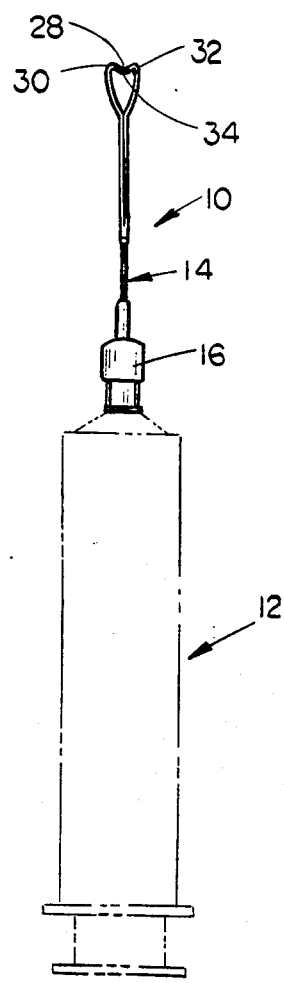
FIG. 1 is a plan view of the irrigating vectis of this invention with the broken lines indicating the irrigating syringe to which the vectis is attached.

An irrigating vectis is described which is conveniently used with a single hand to enable the vectis to be positioned behind the upper portion of the nucleus of the lens during cataract surgery. The vectis comprises an elongated shank portion having means at one end thereof which is connected to an irrigating syringe. The other end of the shank portion is provided with a closed loop portion defined by first and second loop members which extend from the shank portion in a diverging relationship. An end portion extends between the first and second loop portions and has bulged portions at its ends with an indented portion positioned therebetween. Irrigating holes are provided in the end portion to enable the irrigating fluid to be discharged therethrough.

DESCRIPTION OF THE PREFERRED EMBODIMENT

The irrigating vectis of this invention is referred to generally by the reference numeral 10 while the reference numeral 12 refers to a conventional irrigating syringe adapted to be connected thereto as will be described in more detail hereinafter. Vectis 10 generally includes an elongated shank portion 14 having a sleeve connector 16 at one end thereof which is adapted to be detachably secured to the syringe 12. Shank portion 14 includes a pair of hollow shank members 18 and 20 through which the irrigating fluid is forced.

Figure 2:
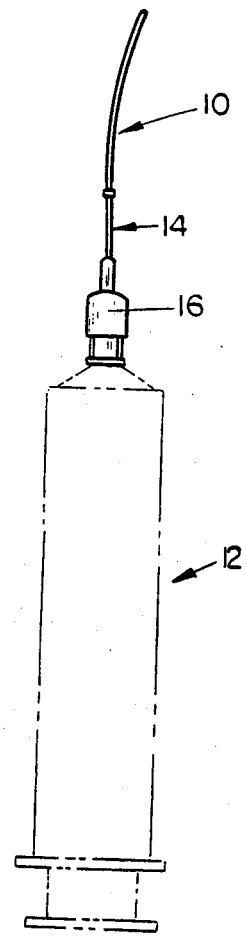
FIG. 2 is a side view of the vectis.
Figure 3:
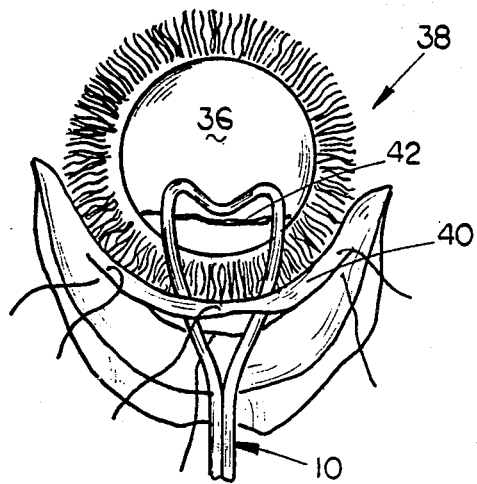
FIG. 3 is a front elevational view illustrating the vectis of this invention being used during cataract surgery, as viewed by the surgeon who is positioned at the patient's head.

The numeral 22 refers to a closed loop portion in communication with the shank portions 18 and 20. Loop portion 22 is comprised of loop members 24 and 26 which extend from shank portion 14 in a diverging relationship as best illustrated in FIG. 3. End portion 28 extends between the ends of loop members 24 and 26 and is provided with bulged portions 30 and 32 at the ends thereof and an indented portion 34 positioned therebetween. Irrigating holes are provided in end portion 28 to enable the irrigating fluid or solution to be discharged outwardly therefrom behind the nucleus of the lens 36 of the eye 38 illustrated in FIG. 3. FIG. 2 illustrates the fact that the vectis is curved along its length to facilitate the insertion of the loop portion 22 behind the upper portion of the nucleus of the lens as will be described in more detail hereinafter.

Figure 4:
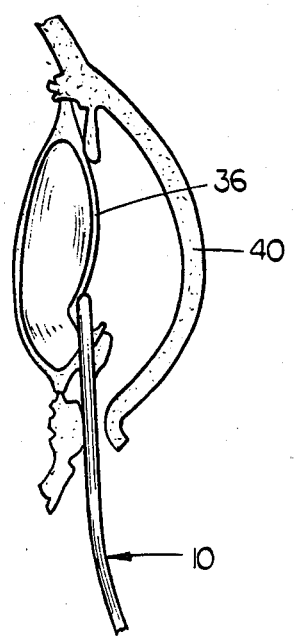
FIG. 4 is a sectional view corresponding to FIG. 3.
Figure 5:
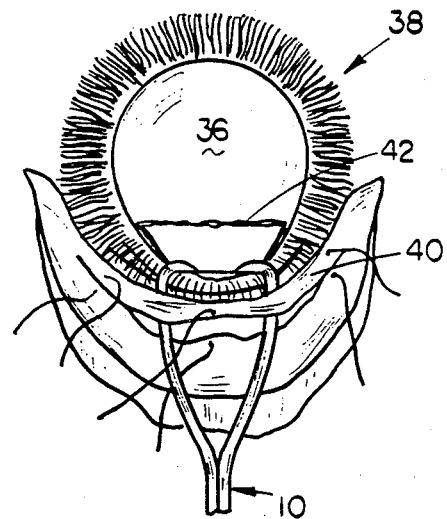
FIG. 5 is a view similar to FIG. 3 except that the vectis has been moved upwardly relative to the lens from the position of FIG. 3 and which shows the iris being retracted.
Figure 6:
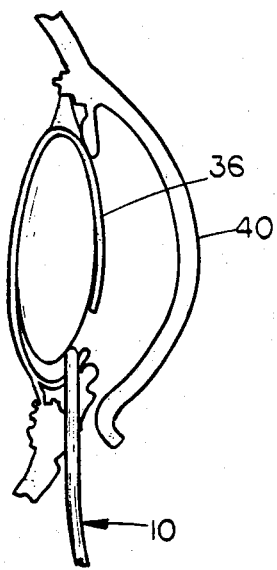
FIG. 6 is a sectional view corresponding to FIG. 5.
Figure 7:
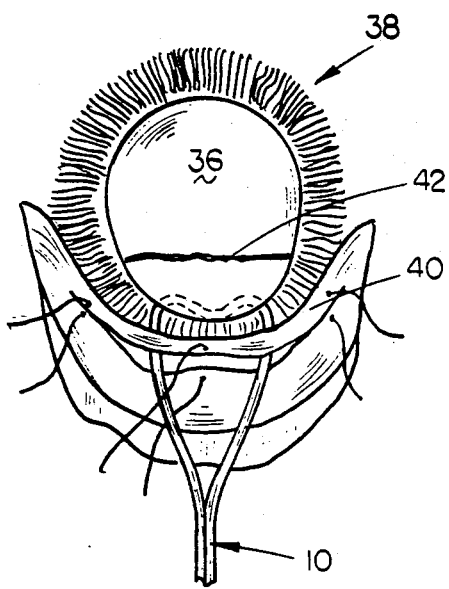
FIG. 7 is a view similar to FIGS. 3 and 5 except that the vectis has been moved downwardly behind the upper portion of the nucleus of the lens.
Figure 8:
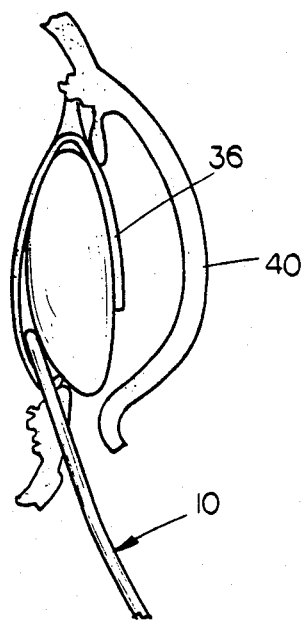
FIG. 8 is a sectional view corresponding to FIG. 7.

In use, the vectis 10 is connected to the syringe 12 in conventional fashion. For purposes of description, in FIGS. 3-8 inclusive, that portion of the eye closest to the lower portion of the drawings is the upper portion of the eye. An incision is first formed in the cornea 40 to permit the cornea to be pulled downwardly and outwardly by means of forceps or the like. An incision 42 is then created in the lens capsule. The end portion 28 of the vectis 10 is then initially positioned on the upper exterior surface of the lens 36 as illustrated in FIGS. 3 and 4. A small amount of pressure is then applied to the lens through the vectis to cause the lens 36 to be forced inwardly. The vectis 10 is then moved upwardly relative to the eye which causes the lens to slightly bulge or protrude outwardly through the indented portion 34. As the indented portion 34 reaches the upper portion of the lens 36, the lens tends to further protrude outwardly between the bulge portions 30 and 32 which enables the end portion 28 to be moved downwardly behind the upper portion of the nucleus of the lens as irrigating fluid is discharged through the irrigating holes in the vectis. The discharge of the irrigating fluid assists in the separation or extraction of the nucleus of the lens. The vectis is moved downwardly behind the nucleus of the lens as the irrigating fluid is discharged therefrom to complete the separation or extraction of the nucleus as illustrated in FIGS. 7 and 8. A very important feature of the irrigating vectis is that the design of the end portion 28 not only permits the vectis to be inserted behind the upper portion of the nucleus but it also causes the iris 42 to be retracted as illustrated in FIG. 5. The retraction of the iris 42 by the vectis as the lens bulges outwardly between the bulge portions 30 and 32 permits the vectis to be inserted behind the upper portion of the lens nucleus with a single hand. In the design of the conventional irrigating vectis, the iris must be retracted with another instrument.

Thus it can be seen that a novel irrigating vectis has been provided which enhances the extraction or removal of cataracts. It can also be seen that the unique configuration of the end portion of the vectis enables the vectis to be positioned behind the upper portion of the lens nucleus with a single hand due to the design of the vectis.

Thus it can be seen that the invention accomplishes at least all of its stated objectives.

I claim:

1. An irrigating vectis, comprising, an elongated shank portion having means on one end thereof for connection to an irrigating syringe, and an irrigating loop portion at the other end of said shank portion, said loop portion having an inwardly indented portion at the end thereof, said irrigating loop portion having irrigating apertures formed therein to enable irrigation fluid to be discharged outwardly therefrom, said loop portion comprising first and second loop members which extend from said shank portion in a diverging relationship, and an end portion extending between said first and second loop portions, said end portion having bulged portions at its end, said indented portions being positioned between said bulged portions.

* * * * *